United States Patent [19]

Denzel et al.

[11] 4,202,899

[45] May 13, 1980

[54] 8H-PYRAZOLO[1,5-A]PYRAZOLO[4',3':5,6-]PYRIDO[3,4-E]PYRIMIDINE

[75] Inventors: Theodor Denzel, Regensburg; Hans Hoehn, Tegernheim, both of Fed. Rep. of Germany

[73] Assignee: E. R. Squibb & Sons, Inc., Princeton, N.J.

[21] Appl. No.: 679,121

[22] Filed: Apr. 21, 1976

[51] Int. Cl.² .................. A61K 31/505; C07D 471/22; C07D 487/22
[52] U.S. Cl. ...................... 424/251; 544/60; 544/115; 544/238; 544/247
[58] Field of Search .................. 260/256.4 F, 256.5 R; 424/251; 544/247

[56] References Cited
U.S. PATENT DOCUMENTS 3,894,021  7/1975  Denzel et al. ................. 260/256.4 F

*Primary Examiner*—Donald G. Daus
*Assistant Examiner*—James H. Turnipseed

*Attorney, Agent, or Firm*—Lawrence S. Levinson; Dale Lovercheck; Merle J. Smith

[57] ABSTRACT

New derivatives of 8H-pyrazolo[1,5-a]pyrazolo[4',3':5,6]-pyrido[3,4-e]pyrimidine have the general formula

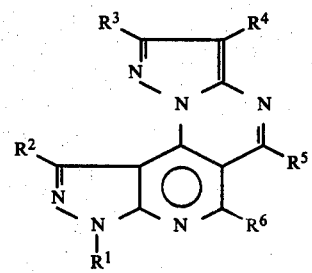

The compounds are useful as anti-inflammatory agents and central nervous system depressants.

24 Claims, No Drawings

8H-PYRAZOLO[1,5-A]PYRAZOLO[4',3':5,6-]PYRIDO[3,4-E]PYRIMIDINE

SUMMARY OF THE INVENTION

This invention relates to new derivatives of 8H-pyrazolo[1,5-a]pyrazolo[4',3':5,6]pyrido[3,4-e]pyrimidine and salts thereof. These new compounds have the general formula

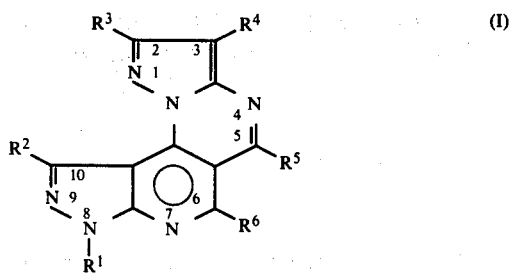

$R^1$ is hydrogen, lower alkyl, phenyl, phenyl-lower alkylene, benzoyl or substituted benzoyl.

$R^2$ and $R^3$ each is hydrogen, lower alkyl or phenyl.

$R^4$ is hydrogen, lower alkyl, phenyl, carboxy or lower alkoxycarbonyl.

$R^5$ is lower alkoxy, substituted lower alkoxy wherein the substituent is

phenyl-lower alkoxy, phenyloxy, substituted phenyloxy wherein the phenyl ring bears one or two simple substituents including lower alkyl, halogen or trifluoromethyl (preferably only one), halo, the group

or the group $-S-R^9$.

$R^6$ is hydrogen or lower alkyl.

$R^7$ is hydrogen, lower alkyl or substituted lower alkyl wherein the lower alkyl substituent is

phenyl or substituted phenyl wherein the phenyl wherein the phenyl substituent is halogen, lower alkyl or trifluoromethyl, $R^8$ is hydrogen or lower alkyl. When $R^7$ is substituted lower alkyl, $R^8$ is preferably hydrogen. In addition $R^7$ and $R^8$ together with the nitrogen may form an unsubstituted or substituted heterocyclic radical including pyrrolidino, morpholino, thiamorpholino, piperidino, pyrazolyl, dihydropyridazinyl or piperazinyl wherein the substituent on the heterocycle is lower alkyl or hydroxy-lower alkyl.

$R^9$, $R^{10}$ and $R^{11}$ each is hydrogen or lower alkyl.

DETAILED DESCRIPTION OF THE INVENTION

The various groups represented by the symbols are of the following types and have the same meanings throughout this specification:

The lower alkyl groups are straight or branched chain hydrocarbon groups having up to seven carbon atoms like methyl, ethyl, propyl, isopropyl, butyl, isobutyl, t-butyl, pentyl and the like. The lower alkylene groups are divalent radicals of the same kind. Examples of the phenyl-lower alkylene groups are benzyl, phenethyl, phenylisopropyl and the like. The $C_1$-$C_4$ and especially the $C_1$-$C_2$ lower alkyl and lower alkylene groups are preferred. The lower alkoxy groups are of the same type. The $C_1$-$C_4$ and $C_1$-$C_2$ groups are similarly preferred and especially preferred groups, respectively.

The substituted phenyloxy and substituted benzoyl groups (i.e., $R^{12}$-phenyloxy, $R^{12}$-benzoyl) are simply substituted groups bearing on the phenyl ring one or two (preferably one), lower alkyl or trifluoromethyl groups ($R^{12}$), for example, p-chlorophenyloxy, o-chlorophenyloxy, p-bromophenyloxy, m-chlorophenyloxy, m-bromophenyloxy, p-tolyloxy, o-tolyloxy, o-ethylphenyloxy, p-trifluoromethylphenyloxy, 3,4-dichlorophenyloxy, 3,5-dimethylphenyloxy, p-bromobenzoyl, m-bromobenzoyl, 3,5-dichlorobenzoyl, p-methylbenzoyl, o-ethylbenzoyl, p-trifluoromethylbenzoyl and the like. Chlorine, bromine and methyl are the preferred substituents (only one) in both instances.

The halogens in each instance are the four common halogens but chlorine and bromine, especially chlorine, are preferred.

The amino group

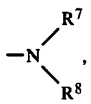

wherein $R^7$ and $R^8$ each represents hydrogen or lower alkyl include the amino group, lower alkylamino groups like methylamino, ethylamino, propylamino, isopropylamino, butylamino, etc., and di-lower alkylamino groups like dimethylamino, diethylamino, methylethylamino, dipropylamino, dibutylamino and the like (preferably, but not necessarily, both lower alkyl groups are the same in a given compound). $R^7$ and $R^8$ can also join with the nitrogen to form one of the heterocyclic radicals pyrrolidino, morpholino, thiamorpholino, piperidino, pyrazolyl, dihydropyridazinyl or piperazinyl. These heterocyclic radicals may be unsubstituted or substituted with a lower alkyl or hydroxylower alkyl group ($R^{13}$). The preferred heterocyclics are piperidino, morpholino and 4-methylpiperazino.

The substituted lower alkoxy groups represented by $R^5$ and the substituted lower alkylamino groups represented by $R^7$ may bear an amino group

as described above resulting in $R^5$ substituents which are amino-lower alkoxy groups

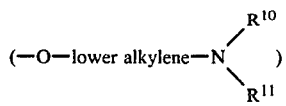

and amino-lower alkyleneamino groups

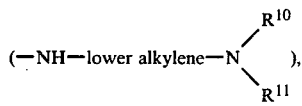

respectively, including, for example, aminomethoxy, aminoethoxy, aminopropoxy, methylaminoethoxy, ethylaminoethoxy, ethylaminopropoxy, dimethylaminomethoxy, dimethylaminoethoxy, dimethylaminopropoxy, diethylaminoethoxy, dimethylaminobutoxy, diethylaminopropoxy, aminoethylamino, aminopropylamino, methylaminopropylamino, ethylaminoethylamino, dimethylaminomethylamino, diethylaminomethylamino, dimethylaminoethylamino, diethylaminoethylamino, dimethylaminopropylamino, and the like. Preferred are those groups wherein the lower alkyl and lower alkylene groups have up to 4 carbons, especially 1 to 2 carbons. Especially preferred group of this type are di-lower alkylamino-lower alkoxy, especially dimethylaminopropoxy and di-lower alkylamino-lower alkyleneamino, especially dimethylaminopropylamino.

Preferred groups of compounds of formula I are those wherein $R^1$ is hydrogen or lower alkyl, especially the latter and most especially ethyl; $R^2$ is hydrogen or lower alkyl, especially hydrogen; $R^3$ is hydrogen or lower alkyl, especially methyl; $R^4$ is hydrogen or lower alkoxycarbonyl, especially ethoxycarbonyl; $R^5$ is amino, mercapto, lower alkylmercapto, especially methylmercapto, lower alkylamino, especially $C_1$–$C_4$-lower alkylamino, lower alkoxy, especially $C_1$–$C_5$-lower alkoxy, di(lower alkyl)amino, especially $C_1$–$C_4$-di(lower alkyl)amino, di(lower alkyl)amino-lower alkylamino, especially wherein the lower alkyl groups are $C_1$–$C_4$ and most especially dimethylaminoethylamino and dimethylaminopropylamino, or di(lower alkyl)amino-lower alkoxy, especially wherein the lower alkyl and lower alkoxy groups are $C_1$–$C_4$ and most especially dimethylaminopropoxy. $R^6$ is hydrogen or lower alkyl, especially hydrogen.

The products of the examples are representative of the various compounds of this invention and constitute especially preferred embodiments.

The new compounds of formula I are formed by the following series of reactions. The symbols in the structural formulas have the same meaning as previously described.

A 4-hydrazinopyrazolo[3,4-b]pyridine-5-carboxylic acid ester of the formula

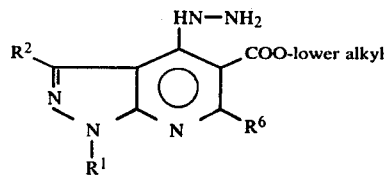

(produced according to the procedure given in U.S. Pat. No. 3,761,487, Sept. 25, 1973) is made to react with a 3-aminocrotonic acid nitrile of the formula

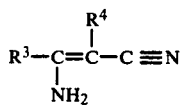

or with an alkoxymethylene compound of the formula

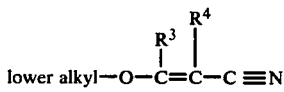

in a high boiling alcohol like n-butyl alcohol or n-amyl alcohol, or the like, at about reflux temperature.

By this reaction a compound of the formula

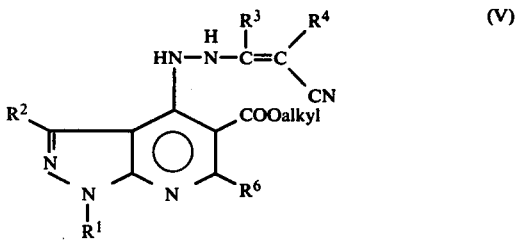

is formed.

Treatment of the compound of formula V with a base, e.g., an alkali metal alkoxide like sodium ethoxide, potassium ethoxide or the like in alcoholic solution or with a Lewis acid like zinc chloride, boron trifluoride or the like in a solvent like acetic acid yields a compound of the formula

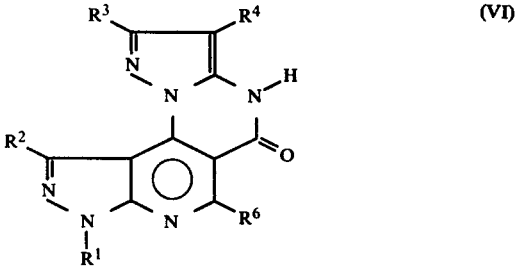

Reaction of the compound of formula VI with a chlorinating agent like phosphorus oxychloride, or phosphorus pentachloride results in the formation of a compound of the formula

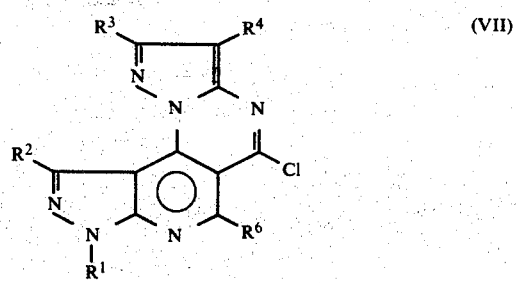

(VII)

Compounds of formula I wherein $R^5$ is lower alkoxy or amino-lower alkoxy are now produced by reaction of the compound of formula VII with an alcoholate of the formula

$$R^{12}-O-Me \qquad (VIII)$$

wherein Me is an alkali metal like sodium or potassium and $R^{12}$ is lower alkyl or amino-lower alkyl

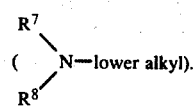

$$( \underset{R^8}{\overset{R^7}{\diagdown}} N-\text{lower alkyl}).$$

Compounds of formula I wherein $R^5$ is lower alkylthio are obtained by reaction of a compound of formula VII with an alkali metalmercaptide of the formula

$$R^{12}-S-Me \qquad (IX)$$

wherein Me is again an alkali metal like sodium or potassium and $R^{12}$ is lower alkyl. Compounds of formula I wherein $R^5$ is mercapto are obtained by reaction of a compound of formula VI with an alkali metal sulfide like sodium sulfide. Compounds of formula I wherein $R^5$ is an amino group or amino-lower alkylene group are produced by reaction of a compound of formula VII with an amine of the formula

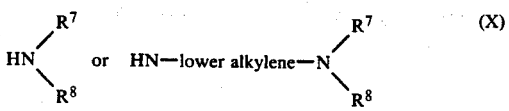

$$HN \underset{R^8}{\overset{R^7}{\diagup}} \quad \text{or} \quad HN-\text{lower alkylene}-N\underset{R^8}{\overset{R^7}{\diagup}} \qquad (X)$$

at elevated temperatures.

When $R^4$ is lower alkoxycarbonyl, the free carboxylic acid is obtained by hydrolysis, e.g., with a base like sodium hydroxide.

The new compounds of formula I form salts which are also part of this invention. The salts include acid addition salts, particularly the non-toxic, physiologically acceptable members. These salts are formed by reaction with one or more equivalents of a variety of inorganic and organic acids providing acid addition salts including, for example, hydrohalides (especially hydrochloride and hydrobromide), sulfate, nitrate, borate, phosphate, oxalate, tartrate, maleate, citrate, acetate, ascorbate, succinate, aryl- and alkanesulfonates like benzenesulfonate, methanesulfonate, cyclohexanesulfamate and toluenesulfonate, etc. The acid addition salts frequently provide a convenient means for isolating the product, e.g., by forming and precipitating a salt (which is not necessarily non-toxic) in an appropriate medium in which the salt is insoluble, then after separation of the salt, neutralizing with a base such as barium hydroxide or sodium hydroxide, to obtain the free base of formula I. Other salts can then be formed from the free base by reaction with an equivalent or more of acid containing the desired anion.

Additional experimental details are found in the examples.

The new compounds of this invention have central nervous system depressant activity and can be used as psychotropic agents, e.g., as ataractic agents for the relief of anxiety and tension states, for example, in mice, cats, rats, dogs and other mammalian species. For this purpose a compound or mixture of compounds of formula I, or non-toxic, physiologically acceptable acid addition salt thereof, is preferably administered orally, but parenteral routes such as subcutaneously, intramuscularly, intravenously or intraperitoneally in the described dosages, can also be employed. A single dose, or preferably 2 to 4 divided daily doses, provided on a basis of about 5 to 50 mg. per kilogram per day, preferably about 10 to 25 mg. per kilogram per day, is appropriate.

The new compounds of this invention also have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 1 to 50 mg/kg/day, preferably 2 to 15 mg/kg/day, in single or 2 to 4 divided doses, as indicated by the carageenan edema or delayed hypersensitivity skin reaction tests in rats. They can also be used topically.

The compounds of the invention can be utilized by formulation in compositions such as tablets, capsules or elixirs for oral administration or in sterile solutions or suspensions for parenteral administration. About 10 to 300 mg. of a compound or mixture of compounds of formula I or physiologically acceptable acid addition salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate, a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup or elixir may contain the active compound, sucrose as a sweetening agent, methyl and propyl parabens as preservatives, a dye and a flavoring such as cherry or orange flavor. Of course, any material used in preparing the dosage unit should be pharmaceutically pure and substantially non-toxic in the amounts employed.

For topical administration as an anti-inflammatory agent, a conventional lotion, ointment or cream containing about 0.1 to 3 percent by weight of a compound of formula I or its salt is formulated.

The following examples are illustrative of the invention and constitute especially preferred embodiments. They also serve as models for the preparation of other members of the group which can be produced by suitable substitution of starting materials. All temperatures are in degrees celsius.

EXAMPLE 1

N-Butyl-8-ethyl-2-methyl-8H-pyrazolo[1,5-a]pyrazolo[4',3':5,6]pyrido[3,4-e]pyrimidin-5-amine (a)
4-[2-(2-Cyano-1-methylethylidene)hydrazino]-1-ethyl-1H-pyrazolo[3,4-b]pyridine-5-carboxylic acid, ethyl ester 249 g of 1-ethyl-4-hydrazino-1H-pyrazolo[3,4-b]-pyridine-5-carboxylic acid, ethyl ester (1 mol) and 82 g of 3-aminocrotononitrile (1 mol) are heated together in 1.5 liters of butyl alcohol with stirring for 24 hours. The solvent is removed in vacuo and the residual 4-[2-(2-cyano-1-methylethylidene)hydrazino]-1-ethyl-1H-pyrazolo[3,4-b]pyridine-5-carboxylic acid, ethyl ester is recrystallized from alcohol, yield 309 g (80%); m.p. 190°-191°.

(b)
8-Ethyl-2-methyl-4H-pyrazolo[1,5-a]pyrazolo[4',3':5,6]-pyrido[3,4-e]pyrimidin-5(8H)-one 309 g of 4-[2-(2-cyano-1-methylethylidene)hydrazino]-1-ethyl-1H-pyrazolo[3,4-e]pyridine-5-carboxylic acid, ethyl ester (0.8 mol) are refluxed with stirring in 1 liter of acetic acid, containing 50 g of zinc chloride, for 24 hours. The solution is cooled to room temperature and after addition of about 1 liter of cold water, 8-ethyl-2-methyl-4H-pyrazolo[1,5-a]pyrazolo[4',3':5,6-]pyrido[3,4-e]pyrimidin5-(8H)-one crystallizes and is filtered off. Purification of the compound is accomplished by dissolving in the theoretical amount of aqueous sodium hydroxide and acidifying the solution with acetic acid, yield 161 g (75%), m.p. 285°-286°.

(c)
5-Chloro-8-ethyl-2-methyl-8H-pyrazolo[1,5-a]pyrazolo[4',3':5,6]pyrido[3,4-e]pyrimidine 161 g of 8-ethyl-2-methyl-4H-pyrazolo[1,5-a]pyrazolo[4',3':5,6]pyrido[3,4e]pyrimidin-5(8H)-one (0.06 mol) are heated with stirring in 1 liter of phosphorus oxychloride at 80° for 48 hours. The mixture is decomposed by pouring onto crushed ice. The 5-chloro-8-ethyl-2-methyl-8H-pyrazolo[1,5-a]pyrazolo[4',3':5,6]pyrido[3,4-e]pyrimidine is filtered off and recrystallized from butyl alcohol, yield 148 g (86%); m.p. 179°-180°.

(d)
N-Butyl-8-ethyl-2-methyl-8H-pyrazolo[1,5-a]pyrazolo[4',3':5,6]pyrido[3,4-e]pyrimidin-5-amine 5.7 g of 5-chloro-8-ethyl-2-methyl-8H-pyrazolo[1,5-a]-pyrazolo[4',3':5,6]pyrido[3,4-e]pyrimidine (0.02 mol) are dissolved in 50 ml of dry alcohol. After addition of 1.5 g of n-butylamine, the mixture is heated at reflux temperature with stirring for 12 hours. The solvent is removed and the crystalline residue is treated with water. The N-butyl-8-ethyl-2-methyl-8H-pyrazolo[1,5-a]pyrazolo[4',3':5,6]pyrido[4,3e]pyrimidin-5-amine is filtered off and recrystallized from ethyl acetate, yield 5 g (77%); m.p. 160°-162°.

EXAMPLE 2

8-Ethyl-2-methyl-N-(1-methylpropyl)-8H-pyrazolo[1,5-a]pyrazolo[4',3':5,6]pyrido[3,4-e]pyrimidin-5-amine, hydrate (1:1)

By substituting 1-methylpropylamine for the n-butylamine in the procedure of Example 1d, 8-ethyl-2-methyl-N-(1-methylpropyl)-8H-pyrazolo[1,5-a]pyrazolo[4',3':5,6]pyrido[3,4-e]-pyrimidin-5-amine, hydrate (1:1) is obtained in 81% yield, m.p. 94°-97° (alcohol).

EXAMPLE 3

8-Ethyl-2-methyl-N-(1-methylethyl)-8H-pyrazolo[1,5-a]pyrazolo[4',3':5,6]pyrido[3,4-e]pyrimidin-5-amine By substituting 1-methylethylamine, for the n-butylamine in the procedure of Example 1d, 8-ethyl-2-methyl-N-(1-methylethyl)-8H-pyrazolo[1,5a]pyrazolo]4',3': 5,6]pyrido[3,4-e]pyrimidin-5-amine is obtained, yield 78%; m.p. 98°-100° (alcohol).

EXAMPLE 4

N-[3-(Dimethylamino)propyl]-8-ethyl-2-methyl-8H-pyrazolo[1,5-a]pyrazolo[4',3':5,6]pyrido[3,4-e]pyrimidin-5-amine 2.9 g of 5-chloro-8-ethyl-2-methyl-8H-pyrazolo[1,5-a]-pyrazolo[4',3':5,6]pyrido[3,4-e]pyrimidine (0.01 mol) are dissolved in 30 ml of alcohol. 2.5 g of 3-(dimethylamino)propyl-1-amine are added and the mixture is refluxed for 5 hours. The solvent is distilled off in vacuo and the crystalline residue extracted twice with 50 ml portions of ethyl acetate. The solvent is removed until the volume is about 20 ml and then cooled. N-[3-(dimethylamino)propyl]-8-ethyl-2-methyl-8H-pyrazolo[1,5-a]pyrazolo[4',3':5,6]pyrido[3,4-e]pyrimidin-5-amine crystallizes and is filtered off, yield 2.8 g (80%); m.p. 178°-179° (ethyl acetate).

EXAMPLE 5

N-[2-(Dimethylamino)ethyl]-8-ethyl-2-methyl-8H-pyrazolo[1,5a]pyrazolo[4',3':5,6]pyrido[3,4-e]pyrimidin-5-amine By substituting 2-(dimethylamino)ethyl-1-amine for the 3-(dimethylamino)propyl-1-amine in the procedure of Example 4, N-[2-(dimethylamino)ethyl]-8-ethyl-2-methyl-8H-pyrazolo[1,5-a]pyrazolo[4',3':5,6-]pyrido[3,4-e]pyrimidin-5-amine is formed, yield 75%; m.p. 124°-126° (ethyl acetate).

EXAMPLE 6

8-Ethyl-2-methyl-5-(4-methyl-1-piperazinyl)-8H-pyrazolo[1,5a]pyrazolo[4',3':5,6]pyrido[3,4e]pyrimidine By substituting 4-methylpiperazine for the 3-(dimethylamino)propyl-1-amine in the procedure of Example 4, 8-ethyl-2-methyl-5-(4-methyl-1-piperazinyl)-8H-pyrazolo[1,5-a]-pyrazolo[4',3':5,6]pyrido[3,4-e]pyrimidine is formed in 69% yield; m.p. 167°-169° (ethyl acetate).

EXAMPLE 7

8-Ethyl-2-methyl-5-(1-piperidinyl)-8H-pyrazolo[1,5-a]pyrazolo[4',3':5,6]pyrido[3,4-e]pyrimidine By substituting piperidine for the 3-(dimethylamino)-propyl-1-amine in the procedure of Example 4, 8-ethyl-2-methyl-5-(1-piperidinyl)-8H-pyrazolo[1,5-a]pyrazolo[4'3,':5,6]pyrido[3,4-e]pyrimidine is obtained, yield 71%; m.p. 176°–177° (alcohol).

EXAMPLE 8

8-Ethyl-2-methyl-5-(4-morpholinyl)-8H-pyrazolo[1,5a]pyrazolo[4',3':5,6]pyrido[3,4-e]pyrimidine By substituting morpholine for 3-(dimethylamino)-propyl-1-amine in the procedure of Example 4, 8-ethyl-2-methyl-5-(4-morpholinyl)8H-pyrazolo[1,5-a]pyrazolo[4',3':5,6]pyrido[3,4-e]pyrimidine is obtained, yield 76%; m.p. 179°–180° (alcohol).

EXAMPLE 9

8-Ethyl-2-methyl-N-[3-(trifluoromethyl)phenyl]-8H-pyrazolo[1,5-a]pyrazolo[4',3':5,6]pyrido[3,4-e]pyrimidin-5-amine 5.8 g of 5-chloro-8-ethyl-2-methyl-8H-pyrazolo[1,5-a]pyrazolo[4',3':5,6]pyrido[3,4-e]pyrimidine (0.02 mol), 3 g of triethylamine and 3.3 g of 3-trifluoromethylaniline are refluxed in butyl alcohol for 24 hours with stirring. The solvent is removed in vacuo and the residue treated with 20 ml of water and filtered off. Recrystallization from alcohol yields 6 g of 8-ethyl-2-methyl-N-[3-(trifluoromethyl)phenyl]-8H-pyrazolo[1,5-a]pyrazolo[4',3':5,6]pyrido[3,4-e]pyrimidin-5-amine; yield (73%) m.p. 205°–206°.

EXAMPLE 10

N,N,8-Triethyl-2-methyl-8H-pyrazolo[1,5-a]pyrazolo[4',3':5,6]pyrido[3,4-e]pyrimidin-5-amine 8.6 g of 5-chloro-8-ethyl-2-methyl-8H-pyrazolo[1,5-a]pyrazolo[4',3':5,6]pyrido[3,4-e]pyrimidine (0.03 mol) and 7.2 g of diethylamine are suspended in 50 ml of butyl alcohol and heated with stirring in an autoclave for 10 hours at 150°. After this time, the solvent is removed, the residue is treated with water and filtered off. Recrystallization from alcohol yields 8 g (83%) of N,N,8-triethyl-2-methyl-8H-pyrazolo[1,5-a]pyrazolo[4',3':5,6]pyrido[3,4-e]pyrimidin-5-amine; m.p. 106°–108°.

EXAMPLE 11

8-Ethyl-2-methyl-8H-pyrazolo[1,5-a]pyrazolo[4',3':5,6-]pyrido[3,4-e]pyrimidin-5-amine By substituting aqueous ammonia (70%) for the diethylamine in the procedure of Example 10, 8-ethyl-2-methyl-8H-pyrazolo[1,5-a]pyrazolo[4',3':5,6-]pyrido[3,4-e]pyrimidin-5-amine is obtained, yield 69%; m.p. 248°–250° (DMF).

EXAMPLE 12

8-Ethyl-N,2-dimethyl-8H-pyrazolo[1,5-a]pyrazolo[4',3':5,6]pyrido[3,4-e]pyrimidin-5-amine By substituting methylamine for the diethylamine in the procedure of Example 10, 8-ethyl-N,2-dimethyl-8H-pyrazolo[1,5-a]pyrazolo[4',3':5,6]pyrido[3,4-e]pyrimidin-5-amine is obtained, yield 76%; m.p. 254°–255° (butyl alcohol).

EXAMPLE 13

5-(Butylamino)-8-ethyl-8H-pyrazolo[1,5-a]pyrazolo[4',3':5,6]pyrido[3,4-e]pyrimidine-3-carboxylic acid, ethyl ester (a)

4-[2-(Cyano-3-ethoxy-3-oxo-1-propenyl)hydrazino]-1-ethyl-1H-pyrazolo[3,4-b]pyridine-5-carboxylic acid, ethyl ester 249 g of 1-ethyl-4-hydrazino-1H-pyrazolo[3,4-b]-pyridine-5-carboxylic acid, ethyl ester (1 mol) are suspended in 1.5 liters of n-butyl alcohol. The mixture is heated with stirring at reflux temperature. At this point, 169 g of ethoxymethylenecyanoacetic acid, ethyl ester (1 mol), dissolved in 500 ml of warm butyl alcohol, are dropped in. After the addition is completed, heating is continued for 2 hours. The solution is cooled in an ice-bath and the precipitated 4-[2-(2-cyano-3-ethoxy-3-oxo-1-propenyl)hydrazino]-1-ethyl-1H-pyrazolo[3,4-b]pyridine-5-carboxylic acid, ethyl ester is filtered off, yield 351 g (94%); m.p. 170°–172° (butyl alcohol).

(b)

8-Ethyl-5,8-dihydro-5-oxo-4H-pyrazolo[1,5-a]pyrazolo[4',3':5,6]pyrido[3,4-e]pyrimidine-3-carboxylic acid, ethyl ester 351 g of 4-[2-(2-cyano-3-ethoxy-3-oxo-1-propenyl)hydrazino]-1-ethyl-1H-pyrazolo[3,4-b]pyridine-5-carboxylic acid, ethyl ester are heated in 2 liters of acetic acid containing 50 g of zinc chloride for 24 hours. After this time, the solution is cooled and 2 liters of cold water are added. The precipitated 8-ethyl-5,8-dihydro-5-oxo-4H-pyrazolo[1,5-a]pyrazolo[4',3':5,6]pyrido[3,4-e]pyrimidine-3-carboxylic acid, ethyl ester is filtered off and purified by dissolving in the theoretical amount of sodium hydroxide in water and precipitating the compound with acetic acid, yield 256 g (83%); m.p. 263°–265°.

(c)

5-Chloro-8-ethyl-8H-pyrazolo[1,5-a]pyrazolo[4',3':5,6-]pyrido[3,4-e]pyrimidine-3-carboxylic acid, ethyl ester 256 g of 8-ethyl-5,8-dihydro-5-oxo-4H-pyrazolo[1,5-a]pyrazolo[4',3':5,6]pyrido[3,4-e]pyrimidine-3-carboxylic acid, ethyl ester are refluxed in 1 liter of phosphorus oxychloride for 24 hours. The excess phosphorus oxychloride is decomposed by pouring the solution on ice and the crystallized 5-chloro-8-ethyl-8H-pyrazolo[1,5-a]pyrazolo[4', 3':5,6]pyrido[3,4-e]pyrimidine-3-carboxylic acid, ethyl ester is filtered off, yield 245 g (91%); m.p. 170°–172° (butyl alcohol).

(d)

5-(Butylamino)-8-ethyl-8H-pyrazolo[1,5-a]pyrazolo[4',3':5,6]pyrido[3,4-e]pyrimidine-3-carboxylic acid, ethyl ester 3.5 g of 5-chloro-8-ethyl-8H-pyrazolo[1,5-a]pyrazolo[4',3':5,6]pyrido[3,4-e]pyrimidine-3-carboxylic acid, ethyl ester (0.01 mol) and 7.3 g of n-butylamine are refluxed together with 30 ml of alcohol with stirring for 8 hours. The solution is evaporated to dryness and the residue treated with water and filtered off. Recrystallization from ethyl acetate yields 3.2 g (84%) of 5-(n-butylamino)-8-ethyl-8H-pyrazolo[1,5-a]pyrazolo[4',3':5,6]pyrido[3,4-e]pyrimidine-3-carboxylic acid, ethyl ester; m.p. 275°–277°.

EXAMPLE 14

5-[(1-Methylpropyl)amino]-8-ethyl-8H-pyrazolo[1,5a]-pyrazolo[4',3':5,6]pyrido[3,4-e]pyrimidine-3-carboxylic acid, ethyl ester By substituting 1-methylpropylamine for the n-butylamine in the procedure of Example 13d, 5-[(1-methylpropyl)amino]-8-ethyl-8H-pyrazolo[1,5-a]pyrazolo[4',3':5,6]pyrido[3,4-e]pyrimidine-3-carboxylic acid, ethyl ester is obtained, yield 71%; m.p. 94°–97°. Hydrolysis with aqueous sodium hydroxide solution yields the free carboxylic acid.

EXAMPLE 15

8-Ethyl-5-(methylamino)-8H-pyrazolo[1,5-a]pyrazolo[4',3':5,6]pyrido[3,4-e]pyrimidine-3-carboxylic acid, ethyl ester 3.5 g of 5-chloro-8-ethyl-8H-pyrazolo[1,5-a]pyrazolo[4',3':5,6]pyrido[3,4-e]pyrimidine-3-carboxylic acid, ethyl ester (0.01 mol) and 3.5 g of methylamine are heated in 50 ml of alcohol in an autoclave for 10 hours at 100°. The solvent is removed in vacuo and the residue treated with water, filtered off and recrystallized from butyl alcohol, yield 2.9 g (86%); m.p. 321°–322°.

EXAMPLE 16

5-(Diethylamino)-8-ethyl-8H-pyrazolo[1,5-a]pyrazolo[4',3':5,6]pyrido[3,4-e]pyrimidine-3-carboxylic acid, ethyl ester By substituting diethylamine for the methylamine in the procedure of Example 15, 5-(diethylamino)-8-ethyl-8H-pyrazolo[1,5-a]pyrazolo[4',3':5,6]pyrido[3,4-e]pyrimidine-3-carboxylic acid, ethyl ester is formed, yield 73%; m.p. 170°–172° (alcohol).

EXAMPLE 17

5-Amino-8-ethyl-8H-pyrazolo[1,5-a]pyrazolo[4',3':5,6]-pyrido[3,4-e]pyrimidine-3-carboxylic acid, ethyl ester By substituting an equivalent amount of 30% aqueous ammonia for the methylamine in the procedure of Example 15, 5-amino-8-ethyl-8H-pyrazolo[1,5-a]pyrazolo[4',3':5,6]pyrido[3,4-e]pyrimidine-3-carboxylic acid, ethyl ester is formed, yield 68%; m.p. 331°–332° (DMF).

EXAMPLE 18

8-Ethyl-5-(4-methyl-1-piperazinyl)-8H-pyrazolo[1,5-a]pyrazolo[4',3':5,6]pyrido[3,4-e]pyrimidine-3-carboxylic acid, ethyl ester 3.5 g of 5-chloro-8-ethyl-8H-pyrazolo[1,5-a]pyrazolo[4',3':5,6]pyrido[3,4-e]pyrimidine-3-carboxylic acid, ethyl ester (0.01 mol) are dissolved in 20 ml of butanol. 2 g of N-methylpiperazine are added and the solution is refluxed with stirring for 12 hours. After evaporation of the solvent, the residue is extracted three times with 50 ml portions of ethyl acetate. The ethyl acetate is distilled off until the volume is about 30 ml. The 8-ethyl-5-(4-methyl-1-piperazinyl)-8H-pyrazolo[1,5-a]pyrazolo[4',3':5,6]pyrido[3,4-e]pyrimidine-3-carboxylic acid, ethyl ester crystallizes, yield 3.1 g (76%); m.p. 111°–113° (ethyl acetate).

EXAMPLE 19

8-Ethyl-5-(1-piperidinyl)-8H-pyrazolo[1,5-a]pyrazolo[4',3':5,6]pyrido[3,4-e]pyrimidine-3-carboxylic acid, ethyl ester By substituting piperidine for the N-methylpiperazine in the procedure of Example 18, 8-ethyl-5-(1-piperidinyl)-8H-pyrazolo[1,5-a]pyrazolo[4',3':5,6]pyrido[3,4-e]pyrimidine-3-carboxylic acid, ethyl ester is obtained, yield 2.6 g (67%); m.p. 183°–184° (ethyl acetate).

EXAMPLE 20

5-[[3-(Dimethylamino)propyl]amino]-8-ethyl-8H-pyrazolo[1,5-a]pyrazolo[4',3':5,6]pyrido[3,4-e]pyrimidine-3-carboxylic acid, ethyl ester By substituting 3-(dimethylamino)propylamine for the N-methylpiperazine in the procedure of Example 18, 5-[[3-(dimethylamino)propyl]amino]-8-ethyl-8H-pyrazolo[1,5-a]pyrazolo[4',3':5,6]pyrido[3,4-e]pyrimidine-3-carboxylic acid, ethyl ester is obtained, yield 62%; m.p. 212°–215° (ethyl acetate).

EXAMPLE 21

5-[3-(Dimethylamino)propoxy]-8-ethyl-2-methyl-8H-pyrazolo[1,5-a]pyrazolo[4',3':5,6]pyrido[3,4-e]pyrimidine To a suspension of 3.6 g of sodium hydride in 100 ml of dry benzene 15.3 g of 3-(dimethylamino)propanol are added and the mixture is refluxed for 6 hours. After this time, 28.6 g of 5-chloro-8-ethyl-2-methyl-8H-pyrazolo[1,5-a]pyrazolo[4',3':5,6]pyrido[3,4-e]pyrimidine are added in small portions with stirring. The solution is refluxed for 10 hours, and then the solvent is distilled off. The residue is treated with water, filtered off and recrystallized from ethyl acetate, yield 25 g (71%); m.p. 62°–64°.

EXAMPLE 22

5-Butoxy-8-ethyl-2-methyl-8H-pyrazolo[1,5-a]pyrazolo[4',3':5,6]pyrido[3,4-e]pyrimidine By substituting n-butyl alcohol for the 3-(dimethylamino)propanol in the procedure of Example 21, 5-butoxy-8-ethyl-2-methyl-8H-pyrazolo[1,5-a]pyrazolo[4',3':5,6]pyrido[3,4-e]pyrimidine is obtained, yield 71%; m.p. 103°–104° (methanol).

EXAMPLE 23

8-Ethyl-2-methyl-5-(1-methylethoxy)-8H-pyrazolo[1,5-a]pyrazolo[4',3':5,6]pyrido[3,4-e]pyrimidine By substituting 2-propanol for the 3-(dimethylamino)propanol in the procedure of Example 21, 8-ethyl-2-methyl-5-(1-methylethoxy)-8H-pyrazolo[1,5-a]pyrazolo[4',3':5,6]pyrido[3,4-e]pyrimidine is obtained, yield 68%; m.p. 129°–130° (ethyl acetate).

EXAMPLE 24

8-Ethyl-2-methyl-5-(3-methylbutoxy)-8H-pyrazolo[1,5-a]pyrazolo[4',3':5,6]pyrido[3,4-e]pyrimidine By substituting 3-methylbutyl alcohol for the 3-(dimethylamino)propanol in the procedure of Example 21, 8-ethyl-2-methyl-5-(3-methylbutoxy)-8H-pyrazolo[1,5-a]pyrazolo[4',3':5,6]pyrido[3,4-e]pyrimidine is obtained, yield 67%; m.p. 60°–62° (ethyl acetate).

EXAMPLE 25

5-Ethoxy-8-ethyl-2-methyl-8H-pyrazolo[1,5-a]pyrazolo[4',3':5,6]pyrido[3,4-e]pyrimidine 2.3 g of sodium are dissolved in 100 ml of dry alcohol with stirring. The solution is heated at reflux temperature and, at this point, 28.6 g of 5-chloro-8-ethyl-2-methyl-8H-pyrazolo[1,5a]pyrazolo[4',3':5,6]pyrido[3,4-e]pyrimidine are added in small portions. Heating and stirring is continued for 6 hours. The precipitated sodium chloride is filtered off, the solvent is removed and the residual 5-ethoxy-8-ethyl-2-methyl-8H-pyrazolo[1,5-a]pyrazolo[4',3':5,6]pyrido[3,4-e]pyrimidine is recrystallized from methanol, yield 82%; m.p. 142°–144°.

EXAMPLE 26

5-[3-(Dimethylamino)propoxy]-8-ethyl-8H-pyrazolo[1,5-a]pyrazolo[4',3':5,6]pyrido[3,4-e]pyrimidine-3-carboxylic acid, ethyl ester To a suspension of 3.6 g of sodium hydride in 100 ml of dry benzene 15.3 g of 3-(dimethylamino)propanol are added dropwise at reflux temperature with stirring. Heating is continued for 10 hours. After this time, 34.4 g of 5-chloro-8-ethyl-8H-pyrazolo[1,5-a]pyrazolo[4',3':5,6]pyrido[3,4-e]pyrimidine-3-carboxylic acid, ethyl ester are added and the solution is refluxed for 5 additional hours. The solution is evaporated to dryness and the residue is treated with water, filtered off and recrystallized from ethyl acetate. 12 g of 5-[3-(dimethylamino)propoxy]-8-ethyl-8H-pyrazolo[1,5-a]pyrazolo[4',3':5,6]pyrido[3,4-e]pyrimidine-3-carboxylic acid, ethyl ester are obtained (29.3%); m.p. 106°–107°.

EXAMPLE 27

8-Ethyl-5-(3-methylbutoxy)-8H-pyrazolo[1,5-a]pyrazolo[4',3':5,6]pyrido[3,4-e]pyrimidine-3-carboxylic acid, ethyl ester By substituting 3-methylbutyl alcohol for the 3-(dimethylamino)propanol in the procedure of Example 26, 8-ethyl-5-(3-methylbutoxy)-8H-pyrazolo[1,5-a]pyrazolo[4',3':5,6]pyrido[3,4-e]pyrimidine-3-carboxylic acid, ethyl ester is obtained, yield 61%; m.p. 117°–118° (ethyl acetate). Hydrolysis with aqueous sodium hydroxide yields the free carboxylic acid.

EXAMPLE 28

5-Ethoxy-8-ethyl-8H-pyrazolo[1,5-a]pyrazolo[4',3':5,6-]pyrido[3,4-e]pyrimidine-3-carboxylic acid, ethyl ester By substituting for the 5-chloro-8-ethyl-2-methyl-8H-pyrazolo[1,5-a]pyrazolo[4',3':5,6]pyrido[3,4-e]pyrimidine in the procedure of Example 25 5-chloro-8-ethyl-8H-pyrazolo[1,5-a]pyrazolo[4',3':5,6]pyrido[3,4-e]pyrimidine-3-carboxylic acid, ethyl ester, 5-ethoxy-8-ethyl-8H-pyrazolo[1,5-a]pyrazolo[4',3':5,6]pyrido[3,4-e]pyrimidine-3-carboxylic acid, ethyl ester is formed, yield 75%; m.p. 167°–168° (alcohol).

EXAMPLE 29

8-Ethyl-2-methyl-8H-pyrazolo[1,5a]pyrazolo[4',3':5,6-]pyrido[3,4-e]pyrimidine-5-thiol 5.6 g of 5-chloro-8-ethyl-2-methyl-4H-pyrazolo[1,5-a]pyrazolo[4',3':5,6]pyrido[3,4-e]pyrimidine (0.02 mol) are dissolved in 100 ml of dimethylformamide. 2 g of powdered sodium sulfite are added and the mixture is stirred for 1 hour. After this time, the solution is carefully acidified with acetic acid. 8-Ethyl-2-methyl-8H-pyrazolo[1,5-a]pyrazolo[4',3':5,6]pyrido[3,4-e]pyrimidine-5-thiol precipitates and is filtered off, yield 5.1 g (91%); m.p. 320°–322° (DMF).

EXAMPLE 30

8-Ethyl-5-mercapto-8H-pyrazolo[1,5-a]pyrazolo[4',3':5,6]pyrido[3,4-e]pyrimidine-3-carboxylic acid, ethyl ester By substituting for the 8-ethyl-2-methyl-4H-pyrazolo[1,5-a]pyrazolo[4',3':5,6]pyrido[3,4-e]pyrimidin-5(8H)-one in the procedure of Example 29 5-chloro-8-ethyl-8H-pyrazolo[1,5-a]pyrazolo[4',3':5,6-]pyrido[3,4-e]pyrimidine-3-carboxylic acid, ethyl ester, 8-ethyl-5-mercapto-8H-pyrazolo[1,5-a]pyrazolo[4',3':5,6]pyrido[3,4-e]pyrimidine-3-carboxylic acid, ethyl ester is formed, yield 86%; m.p. 238°–240° (DMF).

EXAMPLE 31

8-Ethyl-2-methyl-5-(methylthio)-8H-pyrazolo[1,5a]-pyrazolo[4',3':5,6]pyrido[3,4-e]pyrimidine 5.6 g of 5-chloro-8-ethyl-2-methyl-8H-pyrazolo[1,5-a]pyrazolo[4',3':5,6]pyrido[3,4-e]pyrimidine (0.02 mol) and 3 g of sodium methylmercaptide are refluxed together in 50 ml of dimethylformamide with stirring for 2 hours. The mixture is cooled to room temperature and diluted with 50 ml of water. 8-Ethyl-2-methyl-5-(methylthio)-8H-pyrazolo[1,5-a]pyrazolo[4',3':5,6-]pyrido[3,4-e]pyrimidine is filtered off and recrystalized from butyl alcohol, yield 3.5 g (59%); m.p. 168°–169°.

EXAMPLE 32

N-Butyl-2-methyl-8H-pyrazolo[1,5a]pyrazolo[4',3':5,6-]pyrido[3,4-e]pyrimidin-5-amine, By substituting an equivalent amount of 4-hydrazino-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 a and continuing as in parts b, c and d, 5-chloro-2-methyl-8H-pyrazolo[1,5a]pyrazolo[4',3':5,6]pyrido[3,4-e]pyrimidine and N-butyl-2-methyl-8H-pyrazolo[1,5-a]pyrazolo[4',3':5,6-]pyrido[3,4-e]pyrimidin-5-amine respectively, are obtained.

EXAMPLE 33

N,2,8,10-Tetramethyl-8H-pyrazolo[1,5a]-pyrazolo[4',3':5,6]pyrido[3,4-e]pyrimidin-5-amine By substituting 1,3-dimethyl-4-hydrazino-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 a and proceeding as in parts b and c, and substituting methylamine for the butylamine in part d, 5-chloro-2,8,10-trimethyl-8H-pyrazolo[1,5-a]pyrazolo[4',3':5,6]pyrido[3,4-e]pyrimidine and N,2,8,10-tetramethyl-8H-pyrazolo[1,5-a]pyrazolo[4',3':5,6]pyrido[3,4-e]pyrimidin-5-amine are obtained.

EXAMPLE 34

2,3-Diethyl-8-isopropyl-5-phenoxy-8H-pyrazolo[1,5-a]pyrazolo[4′,3′:5,6]pyrido[3,4-e]pyrimidine By substituting 1-isopropyl-4-hydrazino-1H-pyrazolo[3,4b]pyridine-5-carboxylic acid, ethyl ester for the 1-ethyl-4-hydrazino-1H-pyrazolo[3,4-b]pyridine-5-carboxylic acid, ethyl ester and 3-amino-2-ethyl-2-pentenonitrile for the 3-aminocrotononitrile in the procedure of Example 1 a, proceeding as in parts b and c, then following the procedure of Example 21 but substituting phenol for the 3-(dimethylamino)propanol, 5-chloro-2,3-diethyl-8-isopropyl-8H-pyrazolo[1,5-a]pyrazolo[4′,3′:5,6]pyrido[3,4-e]pyrimidine and 2,3-diethyl-8-isopropyl-5-phenoxy-8H-pyrazolo[1,5-a]pyrazolo[4′,3′:5,6]pyrido[3,4-e]pyrimidine, respectively, are obtained.

EXAMPLE 35

5-(4-Chlorophenyloxy)-10-ethyl-2-methyl-8H-pyrazolo[1,5-a]pyrazolo[4′,3′:5,6]pyrido[3,4-e]pyrimidine By substituting 4-hydrazino-3-ethyl-1H-pyrazolo1H-pyrazolo[3,4-b]pyridine-5-carboxylic acid propyl ester for the 1-ethyl-4-hydrazino-1H-pyrazolo[3,4-b]pyridine-5-carboxylic acid, ethyl ester in the procedure of Example 1 a, proceeding as in parts b and c, then following the procedure of Example 21 but substituting 4-chlorophenol for the 3-(dimethylamino)propanol, 5-chloro-10-ethyl-2-methyl-8H-pyrazolo[1,5-a]pyrazolo[4′,3′:5,6]pyrido[3,4-e]pyrimidine and 5-(4-chlorophenyloxy)-10-ethyl-2-methyl-8H-pyrazolo[1,5-a]pyrazolo[4′,3′:5,6]pyrido[3,4-e]pyrimidine, respectively, are obtained.

EXAMPLE 36

5-Benzyloxy-2-methyl-8-phenyl-8H-pyrazolo[1,5-a]pyrazolo[4′,3′:5,6]pyrido[3,4-e]pyrimidine By substituting 4-hydrazino-1-phenyl-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 a, proceeding as in parts b and c, then proceeding as in Example 21 but substituting phenylmethanol for the 3-(dimethylamino)propanol, 5-chloro-2-methyl-8-phenyl-8H-pyrazolo[1,5-a]pyrazolo[4′,3′:5,6-]pyrido[3,4-e]pyrimidine and 5-benzyloxy-2-methyl-8-phenyl-8H-pyrazolo[1,5-a]pyrazolo[4′,3′:5,6]pyrido[3,4-e]pyrimidine, respectively, are obtained.

EXAMPLE 37

N-Butyl-8-ethyl-2,6-dimethyl-8H-pyrazolo[1,5-a]pyrazolo[4′,3′:5,6]pyrido[3,4-e]pyrimidin-5-amine By substituting 1-ethyl-4-hydrazino-6-methyl-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1, 5-chloro-2,6-dimethyl-8-ethyl-8H-pyrazolo[1,5a]pyrazolo[4′,3′:5,6]pyrido[3,4e]pyrimidine and N-butyl-8-ethyl-2,6-dimethyl-8H-pyrazolo[1,5-a]pyrazolo[4′,3′:5,6]pyrido[3,4-e]pyrimidine-5-amine, respectively, are obtained.

EXAMPLE 38

8-Benzyl-2-methyl-8H-pyrazolo[1,5-a]pyrazolo[4′,3′:5,6]pyrido[3,4-e]pyrimidin-5-thiol By substituting 1-benzyl-4-hydrazino-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 a, proceeding as in part b, then proceeding as in Example 29, 8-benzyl-2-methyl-8H-pyrazolo[1,5-a]pyrazolo[4′,3′:5,6]pyrido[3,4-e]pyrimidine-5-thiol is obtained.

EXAMPLE 39

N-Butyl-8-phenylethyl-3-propyl-8H-pyrazolo[1,5-a]pyrazolo[4′,3′:5,6]pyrido[3,4-e]pyrimidin-5-amine By substituting 1-phenylethyl-4-hydrazino-1H-pyrazolo[3,4-b]pyridine-5-carboxylic acid, methyl ester for the 1-ethyl-4-hydrazino-1H-pyrazolo[3,4-b]pyridine-5-carboxylic acid, ethyl ester and 2-aminomethylenepentanonitrile for the 3-aminocrotonitrile in the procedure of Example 1 a and proceeding as in parts b, c and d, 5-chloro-8-phenylethyl-3-propyl-8H-pyrazolo[1,5-a]pyrazolo[4′,3′:5,6]pyrido[3,4-e]pyrimidine and N-butyl-8-phenylethyl-3-propyl-8H-pyrazolo[1,5-a]pyrazolo[4′,3′:5,6]pyrido[3,4-e]pyrimidin5-amine, respectively, are obtained.

EXAMPLE 40

N-butyl-8-ethyl-2-phenyl-8H-pyrazolo[1,5-a]pyrazolo[4′,3′:5,6]pyrido[3,4-e]pyrimidin-5-amine By substituting 3-amino-3-phenylcrotononitrile for the 3-aminocrotononitrile in the procedure of Example 1 a and proceeding as in parts b, c and d, 5-chloro-8-ethyl-2-phenyl-8H-pyrazolo[1,5-a]pyrazolo[4′,3′:5,6-]pyrido[3,4-e]pyrimidine and N-butyl-8-ethyl-2-phenyl-8H-pyrazolo[1,5-a]pyrazolo[4′,3′:5,6]pyrido[3,4-e]pyrimidin-5-amine, respectively, are obtained.

EXAMPLE 41

8-Benzoyl-2-methyl-8H-pyrazolo[1,5-a]pyrazolo[4′,3′:5,6]pyrido[3,4-e]pyrimidin-5(8H)-one (a)

N-Butyl-8-furfuryl-2-methyl-8H-pyrazolo[1,5-a]pyrazolo[4′,3′:5,6]pyrido[3,4-e]pyrimidin-5-amine By substituting 4-hydrazino-1-furfurylpyrazolo[3,4-b]pyridine-5-carboxylic acid, ethyl ester for the 1-ethyl-4-hydrazino-1H-pyrazolo[3,4-b]pyridine-5-carboxylic acid, ethyl ester in Example 1 a and proceeding as in parts a and b, 8-furfuryl-2-methyl-8H-pyrazolo[1,5-a]pyrazolo[4′,3′:5,6]pyrido[3,4-e]pyrimidin-5(8H)-one is obtained. This compound is now processed as in Example 1, parts c and d to obtain N-butyl-8-furfuryl-2-methyl-8H-pyrazolo[1,5-a]pyrazolo[4′,3′:5,6]pyrido[3,4-e]pyrimidin-5-amine.

(b)

N-Butyl-2-methyl-8H-pyrazolo[1,5-a]pyrazolo[4′,3′:5,6]-pyrido[3,4-e]pyrimidin-5-amine 0.01 mol of N-butyl-8-furfuryl-2-methyl-8H-pyrazolo[1,5-a]pyrazolo[4′,3′:5,6]pyrido[3,4-e]pyrimidin-5-amine is heated in 50 ml of diethyleneglycol dimethyl ether containing 0.01 mol of selenium dioxide at reflux temperature with stirring for two hours. The mixture is filtered hot and evaporated to dryness. N- butyl-2-methyl-8H-pyrazolo[1,5-a]pyrazolo[4',3':5,6-]pyrido[3,4-e]pyrimidin-5-amine remains.

(c)

8-Benzoyl-N-butyl-2-methyl-8H-pyrazolo[1,5-a]pyrazolo[4',3'-5,6]pyrido[3,4-3]pyrimidin-5-amine 0.01 mol of N-butyl-2-methyl-8H-pyrazolo[1,5-a]pyrazolo[4',3':5,6]pyrido[3,4-e]pyrimidin-5-amine and 0.02 mol of benzoyl chloride are stirred overnight in 50 ml of dry pyridine at room temperature. On addition of 50 ml of water, 8-benzoyl-N-butyl-2-methyl-8H-pyrazolo[1,5-a]pyrazolo[4',3':5,6]pyrido[3,4-e]pyrimidin-5-amine is filtered off.

EXAMPLE 42

N-Butyl-2-methyl-8-(4-methylbenzoyl)-8H-pyrazolo[1,5-a]pyrazolo[4',3'-5,6]pyrido[3,4-e]pyrimidin-5-amine By substituting 1-(4-methylbenzoyl)-4-hydrazino-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 a and proceeding as in parts b, c and d, 5-chloro-2-methyl-8-(4-methylbenzoyl)-8H-pyrazolo[1,5-a]pyrazolo[4',3':5,6]pyrido[3,4-e]pyrimidine and N-butyl-2-methyl-8-(4-methylbenzoyl)-8H-pyrazolo[1,5-a]pyrazolo[4',3':5,6]pyrido[3,4-e]pyrimidin-5-amine, respectively, are obtained.

EXAMPLE 43

5-(2-Aminoethoxy)-2,6-dimethyl-8-ethyl-8H-pyrazolo[1,5-a]pyrazolo[4',3':5,6]pyrido[3,4-e]pyrimidine By substituting the 5-chloro-2,6-dimethyl-8-ethyl-8H-pyrazolo[1,5-a]pyrazolo[4',3':5,6]pyrido[3,4-e]pyrimidine obtained in Example 37 in the procedure of Example 21 and substituting ethanolamine for the 3-(dimethylamino)propanol, 5-(2-aminoethoxy)-2,6-dimethyl-8-ethyl-8H-pyrazolo[1,5-a]pyrazolo[4',3':5,6]pyrido[3,4-e]pyrimidine is obtained.

The hydrochloride salt is obtained by treating the above product with ethanolic HCl.

EXAMPLE 44

8-Ethyl-2-methyl-5-[(3-propylamino)propoxy]-8H-pyrazolo[1,5-a]pyrazolo[4',3':5,6]pyrido[3,4-e]pyrimidine By substituting 3-(propylamino)propanol for the 3-(dimethylamino)propanol in the procedure of Example 21, 8-ethyl-2-methyl-5-[(3-propylamino)propoxy]-8H-pyrazolo[1,5-a]pyrazolo[4',3':5,6]pyrido[3,4-e]pyrimidine is obtained.

EXAMPLE 45

8-Ethyl-2-methyl-5-(1-piperazinyl)-8H-pyrazolo[1,5-a]pyrazolo[4',3':5,6]pyrido[3,4-e]pyrimidine By substituting piperazine for the 3-(dimethylamino)propyl-1-amine in the procedure of Example 4, 8-ethyl-2-methyl-5-(1-piperazinyl)-8H-pyrazolo[1,5-a]pyrazolo[4',3':5,6]pyrido[3,4-e]pyrimidine is obtained.

EXAMPLE 46

N-Butyl-8-ethyl-2,3-diphenyl-8H-pyrazolo[1,5-a]pyrazolo[4',3':5,6]pyrido[3,4-e]pyrimidin-5-amine By substituting 3-amino-2,3-diphenylcrotononitrile for the 3-aminocrotononitrile in the procedure of Example 1, 5-chloro-8-ethyl-2,3-diphenyl-8H-pyrazolo[1,5-a]pyrazolo[4',3':5,6]pyrazolo[3,4-e]pyrimidine and N-butyl-8-ethyl-2,3-diphenyl-8H-pyrazolo[1,5-a]pyrazolo[4',3':5,6]pyrido[3,4-e]pyrimidin-5amine, respectively, are obtained.

EXAMPLE 47

8-Ethyl-2-methyl-5-thiamorpholino-8H-pyrazolo[1,5-a]pyrazolo[4',3':5,6]pyrido[3,4-e]pyrimidine By substituting thiamorpholine for the 3-(dimethylamino)propyl-1-amine in the procedure of Example 4, 8-ethyl-2-methyl-5-thiamorpholino-8H-pyrazolo[1,5-a]pyrazolo[4',3':5,6]pyrido[3,4-e]pyrimidine is obtained.

EXAMPLE 48

8-Ethyl-2-methyl-5-(1-pyrazolyl)-8H-pyrazolo[1,5-a]pyrazolo[4',3':5,6]pyrido[3,4-e]pyrimidine By substituting pyrazole for the 3-(dimethylamino)propyl-1-amine in the procedure of Example 4, 8-ethyl-2-methyl-5-(1-pyrazolyl)-8H-pyrazolo[1,5-a]pyrazolo[4',3':5,6]pyrido[3,4-e]pyrimidine is obtained.

EXAMPLE 49

8-Ethyl-2-methyl-5-pyrrolidino-8H-pyrazolo[1,5-a]pyrazolo[4',3':5,6]pyrido[3,4-e]pyrimidine By substituting pyrrolidine for the 3-(dimethylamino)propyl-1-amine in the procedure of Example 4, 8-ethyl-2-methyl-5-pyrrolidino-8H-pyrazolo[1,5-a]pyrazolo[4',3':5,6]pyrido[3,4-e]pyrimidine is obtained.

EXAMPLE 50

8-Ethyl-2-methyl-5-(dihydropyridazin-1-yl)-8H-pyrazolo[1,5-a]pyrazolo[4',3':5,6]pyrido[3,4-e]pyrimidine By substituting dihydropyridazine for the 3-(dimethylamino)propyl-1-amine in the procedure of Example 4, 8-ethyl-2-methyl-5-(dihydropyridazin-1-yl)-8H-pyrazolo[1,5-a]pyrazolo[4',3':5,6]pyrido[3,4-e]pyrimidine is obtained.

EXAMPLE 51

The following ingredients are used to make 1,000 200 mg tablets each containing 100 mg of active ingredient:

| | |
|---|---|
| N-butyl-8-ethyl-2-methyl-8H-pyrazolo-[1,5-a]pyrazolo[4',3':5,6]pyrido-[3,4-e]pyrimidine-5-amine | 100 gm. |
| Polyvinyl pyrrolidone | 7.5 gm. |
| Lactose | 20 gm. |
| Magnesium stearate | 3.5 gm. |
| Corn starch | 17.5 gm. |
| Avicel (microcrystalline cellulose) | 51.5 gm. |

The medicament and lactose are thoroughly admixed. The polyvinyl pyrrolidone is dissolved in ethanol USP to make a 30% solution. This solution is used to granulate the mixture of medicament and lactose. The granulation is passed through a No. 16 screen and air dried. The dried granulation is then passed through a No. 20 screen. To the screened granulate are added the magnesium stearate, Avicel and the corn starch and the mixture is blended. The blend is then compressed into 200 mg. tablets on a standard concave punch. The tablets are then veneer coated with methyl cellulose in a spray pan.

What is claimed is:

1. A compound of the formula

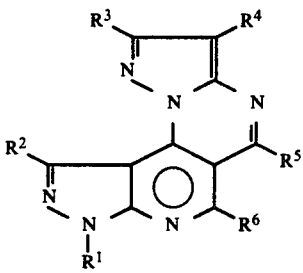

wherein
R¹ is hydrogen, lower alkyl, phenyl, phenyl-lower alkylene, benzoyl or substituted benzoyl wherein the benzoyl substituent is one or two halogens, lower alkyl or trifluoromethyl groups;
R² and R³ each is hydrogen, lower alkyl or phenyl;
R⁴ is hydrogen, lower alkyl, phenyl, carbonyl or lower alkoxycarbonyl;
R⁵ is lower alkoxy, substituted lower alkoxy wherein the substituent is

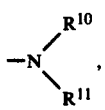

phenyloxy, substituted phenyloxy wherein the phenyl ring bears one or two halogen, lower alkyl or trifluoromethyl groups, halo,

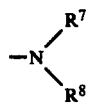

or —S—R⁹,
R⁶ is hydrogen or lower alkyl;
R⁷ is hydrogen, lower alkyl or substituted lower alkyl wherein the substituent is

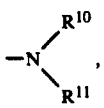

phenyl, substituted phenyl wherein the phenyl substituent is halogen, lower alkyl or trifluoromethyl, and R⁸,
R⁹, R¹⁰ and R¹¹ each is hydrogen or lower alkyl.

2. A compound as in claim 1 wherein R¹, R², R³ and R⁶ each is hydrogen or lower alkyl; R⁴ is hydrogen or lower alkoxycarbonyl; R⁵ is amino, mercapto, lower alkylamino, di(lower alkyl)amino, di(lower alkyl)amino-lower alkylamino or di(lower alkyl)amino-lower alkoxy.

3. A compound as in claim 1 wherein R² and R⁶ each is hydrogen.

4. A compound as in claim 1 wherein R⁵ is lower alkylamino.

5. A compound as in claim 1 wherein R⁵ is lower alkoxy.

6. A compound as in claim 1 wherein R⁵ is di(lower alkyl)amino-lower alkylamino.

7. A compound as in claim 1 wherein R⁵ is di(lower alkyl)amino-lower alkoxy.

8. A compound as in claim 1 wherein R⁵ is halogen.

9. A compound as in claim 1 wherein R⁵ is lower alkylmercapto.

10. A compound as in claim 3 wherein R¹ and R³ each is lower alkyl, R⁴ is hydrogen and R⁵ is lower alkylamino.

11. A compound as in claim 3 wherein R¹ and R³ each is lower alkyl, R⁴ is hydrogen and R⁵ is lower alkoxy.

12. A compound as in claim 1 wherein R¹ is lower alkyl, R² and R⁴ each is hydrogen, R³ is hydrogen or lower alkyl, R⁴ is hydrogen or lower alkoxycarbonyl and R⁵ is halogen.

13. A compound as in claim 1 wherein R¹ is ethyl, R², R⁴ and R⁶ each is hydrogen, R³ is methyl and R⁵ is chloro.

14. A compound as in claim 1 wherein R¹ is ethyl, R², R³ and R⁶ each is hydrogen, R⁴ is ethoxycarbonyl and R⁵ is chloro.

15. A compound as in claim 3 wherein R¹ is ethyl, R³ is methyl, R⁴ is hydrogen and R⁵ is butylamino.

16. A compound as in claim 3 wherein R¹ is ethyl, R³ is methyl, R⁴ is hydrogen and R⁵ is ethoxy.

17. A compound as in claim 3 wherein R¹ is ethyl, R³ is methyl, R⁴ is hydrogen and R⁵ is 3-(dimethylamino)-propylamino.

18. A compound as in claim 3 wherein R¹ is ethyl, R³ is hydrogen, R⁴ is ethoxycarbonyl and R⁵ is 3-(dimethylamino)propylamino.

19. A compound as in claim 3 wherein R¹ is ethyl, R³ is methyl, R⁴ is hydrogen and R⁵ is 3-methylbutoxy.

20. A compound as in claim 3 wherein R¹ is ethyl, R³ is methyl, R⁴ is hydrogen and R⁵ is 1-methylethoxy.

21. A compound as in claim 3 wherein R¹ is ethyl, R³ is methyl, R⁴ is hydrogen and R⁵ is 1-methylethylamino.

22. A composition comprising about 10 to 300 mg. of a compound of claim 1 and a physiologically acceptable carrier therefor.

23. A method for treating inflammatory conditions which comprises administering to a mammal suffering therefrom a composition comprising about 10 to 300 mg. of a compound of claim 1 and a physiologically acceptable carrier therefor.

24. A compound of the formula

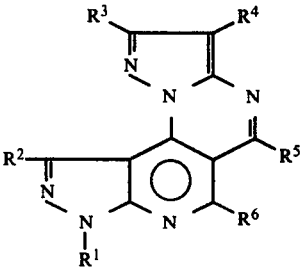

wherein
R¹ is hydrogen, lower alkyl, phenyl, phenyl-lower alkylene, benzoyl or substituted benzoyl wherein the benzoyl substituent is one or two halogens, lower alkyl or trifluoromethyl groups;
R² and R³ each is hydrogen, lower alkyl or phenyl;
R⁴ is hydrogen, lower alkyl, phenyl, carboxy or lower alkoxycarbonyl;

$R^5$ is lower alkoxy substituted lower alkoxy wherein the substituent is

phenyloxy, substituted phenyloxy wherein the phenyl ring bears one or two halogen, lower alkyl or trifluoromethyl groups, halo,

or $-S-R^9$;

$R^6$ is hydrogen or lower alkyl;

$R^7$ is hydrogen, lower alkyl or substituted lower alkyl wherein the substituent is

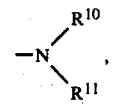

phenyl, substituted phenyl wherein the phenyl substituent is halogen, lower alkyl or trifluoromethyl;

$R^8$, $R^9$, $R^{10}$ and $R^{11}$ each is hydrogen or lower alkyl; and acid addition salts thereof.

* * * * *

UNITED STATES PATENT AND TRADEMARK OFFICE
CERTIFICATE OF CORRECTION

PATENT NO. : 4,202,899
DATED : May 13, 1980
INVENTOR(S) : Theodor Denzel et al.

It is certified that error appears in the above–identified patent and that said Letters Patent are hereby corrected as shown below:

```
Col. 2, line 37, change "group" to -- groups --.
Col. 7, line 48, change "[3,4e]" to -- [3,4-e] --.
Col. 7, line 68, change "[3,4e]" to -- [3,4-e] --.
Col. 15, line 65, change "[3,4e]" to -- [3,4-e] --.
Col. 16, line 28, change "pyrimidin5" to -- pyrimidin-5 --.
Col. 17, line 5, change "[3,4-3]" to -- [3,4-e] --.
Col. 17, line 5, change "[4,3'-5,6]" to -- [4,3':5,6] --.
Col. 17, line 16, change "[4,3'-5,6]" to -- [4,3':5,6] --.
Col. 19, line 22, change "carbonyl" to -- carboxy --.
```

Signed and Sealed this

Ninth Day of September 1980

[SEAL]

Attest:

SIDNEY A. DIAMOND

Attesting Officer    Commissioner of Patents and Trademarks